(12) United States Patent
Bleines (10) Patent No.: US 7,552,101 B2
(45) Date of Patent: Jun. 23, 2009

(54) HEALTH MONITORING SYSTEM IMPLEMENTING MEDICAL DIAGNOSIS

(75) Inventor: Bruno Bleines, Hericy (FR)

(73) Assignee: Vigimedia S.A.S., Rosieres-Pres-Troyes (FR)

( * ) Notice: Subject to any disclaimer, the term of this patent is extended or adjusted under 35 U.S.C. 154(b) by 237 days.

(21) Appl. No.: 10/577,499

(22) PCT Filed: Nov. 2, 2004

(86) PCT No.: PCT/FR2004/050556

§ 371 (c)(1),
(2), (4) Date: Apr. 28, 2006

(87) PCT Pub. No.: WO2005/048160

PCT Pub. Date: May 26, 2005

(65) Prior Publication Data

US 2007/0073520 A1    Mar. 29, 2007

(30) Foreign Application Priority Data

Oct. 31, 2003   (FR) .................................. 03 50760

(51) Int. Cl.
*G06N 5/02*   (2006.01)
(52) U.S. Cl. ....................................... 706/47
(58) Field of Classification Search .................. None
See application file for complete search history.

(56) References Cited

U.S. PATENT DOCUMENTS

| | | | | |
|---|---|---|---|---|
| 5,465,321 A | * | 11/1995 | Smyth .......................... | 706/20 |
| 5,544,308 A | * | 8/1996 | Giordano et al. .............. | 714/26 |
| 5,710,723 A | * | 1/1998 | Hoth et al. ................... | 702/181 |
| 6,741,974 B1 | * | 5/2004 | Harrison et al. ............... | 706/47 |

(Continued)

FOREIGN PATENT DOCUMENTS

JP    1 193 637 A1  *  3/2000

(Continued)

OTHER PUBLICATIONS

A Home Health Monitoring System Including Intelligent Reporting and Alerts Garsden, H.; Basilakis, J.; Celler, B.G.; Huynh, K.; Lovell, N.H; Engineering in Medicine and Biology Society, 2004. IEMBS '04. 26th Annual International Conference of the IEEE vol. 2, 2004 pp. 3151-3154 Digital Object Identifier 10.1109/IEMBS.2004. 1403889.*

(Continued)

*Primary Examiner*—Michael B Holmes
(74) *Attorney, Agent, or Firm*—Kinney & Lange, P.A.

(57) ABSTRACT

The invention relates to a health surveillance system comprising a medical diagnosis which is made by a medically-qualified person (11) in relation to a patient who is being monitored remotely, e.g. at home, via a communication network. The invention is characterised in that the medically-qualified person (11) links medical data (2) to health actions (3) in a server (1) using surveillance rules. The invention is further characterised in that the server (1) programs a remote terminal (9) which is located close to the patient, such that the remote terminal (9) uses an automatism (5) which applies the surveillance rules to the medical data supplied to the terminal by at least one sensor (8) which is associated with the patient and/or by a man/machine interface of the remote terminal (13) and/or by a man/machine interface of a network station (12) and/or by the network (7).

20 Claims, 1 Drawing Sheet

U.S. PATENT DOCUMENTS

| | | | | |
|---|---|---|---|---|
| 6,745,764 B2 * | 6/2004 | Hickle | .................... | 128/203.12 |
| 6,807,965 B1 * | 10/2004 | Hickle | .................... | 128/204.23 |
| 6,838,993 B2 * | 1/2005 | Beiswenger et al. | ..... | 340/573.5 |
| 6,986,347 B2 * | 1/2006 | Hickle | .................... | 128/200.24 |
| 6,999,884 B2 * | 2/2006 | Astley et al. | .................. | 702/56 |
| 7,103,460 B1 * | 9/2006 | Breed | .......................... | 701/29 |
| 7,201,734 B2 * | 4/2007 | Hickle | ........................ | 604/67 |
| 7,247,154 B2 * | 7/2007 | Hickle | ........................ | 604/500 |
| 7,308,894 B2 * | 12/2007 | Hickle | .................... | 128/204.23 |

OTHER PUBLICATIONS

Rule-Based Motor Fault Detection Eren, L.; Onur Baskirt; Devaney, M.J.; Instrumentation and Measurement Technology Conference, 2005. IMTC 2005. Proceedings of the IEEE vol. 2, May 16-19, 2005 pp. 834-837 Digital Object Identifier 10.1109/IMTC.2005. 1604250.*

A formal language approach for multi-sensor Wearable Health-Monitoring Systems Pantelopoulos, A.; Bourbakis, N.; BioInformatics and BioEngineering, 2008. BIBE 2008. 8th IEEE International Conference on Oct. 8-10, 2008 pp. 1-7 Digital Object Identifier 10.1109/BIBE.2008.4696772.*

A central repository for biosignal data Sooyoung Yoo; Dongwoo Rho; Gyeongwoo Cheon; Jinwook Choi; Technology and Applications in Biomedicine, 2008. ITAB 2008. International Conference on May 30-31, 2008 pp. 275-277 Digital Object Identifier 10.1109/ITAB.2008.4570556.*

* cited by examiner

FIG.1

HEALTH MONITORING SYSTEM IMPLEMENTING MEDICAL DIAGNOSIS

1. THE PROBLEM

The portion of remote monitoring in the overall socio-medical care of patients, and especially the maintaining of patients in the home (MPH), is likely to develop and with it the remote monitoring which makes it possible to appreciate a risk situation in the absence of care personnel. The context of remote monitoring of patients, especially with MPH, implies furthermore the use of tools that are not traumatising for the person and that are capable of detecting a possible degradation in his state of health.

Remote monitoring for a patient takes place with recording devices (medical assistance equipment, sensors, camera, etc.) placed in the environment of the patient and which, in the event of an anomaly, sends a signal via a communications network to designated persons in order to come to the aid of the patient. These systems detect crisis situations (example: falls, heart rhythm trouble) in patients for which the risks are identified and which are subject to generally intensive monitoring. On the other hand, they do not apply well to the MPH population which is made up of "fragile" people requiring daily health monitoring that is the least traumatising possible and often non intensive. Most aged people who are monitored via MPH, for which the number is expected to increase considerably in the years to come in all of the western countries, do not show dominant pathologies, which makes it difficult to anticipate crisis phases using only the measurement of a physiologic signal.

2. PRIOR ART

2.1 Remote Alarm

The remote alarm is widely used in MPH, either as a complement to medical equipment, or alone. This terms groups together different devices, fixed or on, activated by the person to trigger the calling of emergency numbers via the STN or GSM network. These devices, although extremely easy to use, have the major disadvantage of not enabling to appreciate the actual seriousness of the situation. Their untimely use, either on purpose or due to an error in manipulation, thus mobilises rescue teams for interventions that are not always justified.

2.2 Smart Sensors

Multisensor devices, referred to as "smart", connected to the patient or placed in his living environment, respectively allow more complete physiological monitoring (electrocardiogram, oxygen saturation, sodium on the skin, etc.) and the appreciation of environmental factors that act on the patient. Among the existing systems, one can note "smart clothing" that incorporates chips (Medes, Nokia, etc.) or home automation experiments carried out by the CNRS of Grenoble. The use of such systems implies a constant on-duty delocalised medical team which interprets the data. Setting up this costly logistics today restricts its application as MPH to acute pathology monitoring.

2.3 Expert Systems

In order to overcome constant health monitoring, expert systems per pathology are being developed. They remotely analyse data coming from the patient (signals, measurements, text) and can return medical advice or alert health professionals. The deterministic approach to these systems restricts their application to patients that have a pathology that is controlled well. The complexity of multiple pathologies cannot today be treated by these methods, which severely limits the use of these expert systems with older people who represent the main population treated as MPH.

Furthermore, the different methods of the prior art presented above have other disadvantages, which are:

i) The information read by the sensors is sent via a communications network in such a way that, if a communications problem prevents the communication between the sensor and the delocalised medical team, the data measured by the sensors cannot be used to warn the patient and/or distinct emergency services (ambulance, doctor) in case of need.

ii) Each sensor sends "raw" data that the on-duty medical team analyses and interprets at a determined frequency, i.e. discontinuously. So, if a health incident occurs between two analyses, there is a risk that this incident be detected only during the second analysis, which results in a loss of time in the reaction implemented by the delocalised on-duty medical team.

Furthermore, if an alarm is associated with the information sent by a sensor, the on-duty medical team is alerted to the health incident as soon as the information provided by the sensor reaches the alarm threshold. In this case, it is necessary to analyse the information previous to the alarm in order to possibly detect pertinent information concerning the diagnosis to be carried out.

So, when an alarm occurs, the on-duty medical team finds itself faced with an emergency situation without being able to systematically place the alarm in the general context of the patient (medical and surgical antecedents, allergies, etc.).

iii) When several sensors are used to provide different information, each piece of information is relative to a specific medical parameter—blood pressure, electrocardiogram (EKG), temperature, etc.

So, the on-duty medical team must analyse each parameter, both individually and in combination with the other parameters, these combinations again increasing the quantity of information that has to be processed by the on-duty delocalised medical team, or even by distinct on-duty teams which, where necessary, may have to consult each other in order to decide and/or trigger a health action.

3. SOLUTION

This invention aims to remedy at least one of the disadvantages mentioned above. It relates to a health monitoring method implementing medical diagnosis established by a person who is medically qualified concerning a patient who is remotely monitored, in particular at his home, and monitored via a communications network, characterised in that:

The medically-qualified person associates medical data with health actions in a server via monitoring rules, The server programs a distant terminal, located near the patient in such a way that the distant terminal implements an automatism applying the monitoring rules to the medical data provided to the terminal by at least one sensor associated with the patient and/or by a man-machine interface of the distant terminal and/or by a man-machine interface of a networked station and/or by the network.

The invention seems to allow a medically-qualified person to truly be aided by automatic means in order to carry out monitoring of a patient remotely monitored according to the diagnosis determined by the medically-qualified person.

In an embodiment the medical data provided to the terminal by a sensor that belongs to the patient and/or by a man-machine interface of the distant terminal and/or by a man-machine interface of a networked station and/or by the network is sent to the medically-qualified person via a communications network so that the latter can take the sent data into account when possibly modifying the monitoring rules associating the data and health actions at the level of the server.

According to one embodiment, at least one sensor and/or man-machine interface is integrated into the distant terminal.

In one embodiment, the monitoring rules are added, modified or eliminated on the server via the communications network automatically or manually.

According to an embodiment, means are associated to the distant terminal to test its communication with the medically-qualified person and/or with a third party so as to ensure the transmission of alerts to this person and/or to this third party when the monitoring rules are implemented.

In one embodiment, the sensor and/or man-machine interface of the distant terminal and/or the man-machine interface of the networked station and/or the network sends data discontinuously to the terminal.

According to one embodiment, different sensors are used to measure several pieces of medical data of distinct categories.

In one embodiment, the sensors under consideration aim at measuring data of at least one of the following categories: blood pressure, heart rhythm, body temperature, skin temperature, sodium content on the skin, kinetic and/or kinematic parameters of the body, blood dosage, analysis of urine and/or stool and/or blood gas, weight, electrocardiogram data, heart sounds, oxygen saturation, thermal image.

In one embodiment, a sensor includes a man-machine interface in order to provide medical data to the terminal via the interface such as: intensity of pain, state of fatigue, alterations in the state of consciousness, difficulties in speaking.

According to one embodiment, means are associated to the man-machine interface of the distant terminal in order to intervene on the server.

In one embodiment, the data sent by the network is relative to data such as results of biological examinations and/or functioning of a piece of equipment connected to the network, in particular home automation equipment for detecting presence, control of access, heating, lighting, openings, fire, flooding, mains cut-off and/or a medical device, relative to an alarm signal or any signal resulting from the transformation of measurements and coming from such a connected device, in particular a pump and/or administration set and/or respirator and/or fall detector or relative to information coming from third-party software, in particular from an expert system, likely to be executed on the terminal or on a machine connected to the terminal, such as software for monitoring self-care haemodialysis and/or for monitoring glycaemia of diabetics and/or monitoring blood pressure.

According to one embodiment, monitoring rules are made available to a medically-qualified person, so that this person may render these monitoring rules operative or inoperative.

In one embodiment, a user provides data to the distant terminal via the network using a piece of equipment that is distinct from said distant terminal, in particular using a terminal that has wireless means of communication of the radiofrequency and/or infrared type.

The invention also relates to a health monitoring station characterized in that it includes means so that a person receives alerts and/or consults the data server via a man-machine interface according to a method that conforms to one of the preceding embodiments.

The invention also relates to a medical station characterized in that it includes means to that a medically-qualified person programs, via a man-machine interface, a distant terminal according to a method that conforms to one of the preceding embodiments.

The invention also relates to a health monitoring server aiming to make it possible to implement a medical diagnosis established by a medically-qualified person pertaining to a patient that is remotely monitored, in particular at his home, and monitored by a communications network, characterised in that:

The server includes means for the medically-qualified person to associate medical data with health actions in a server via monitoring rules, The server includes means for programming a distant terminal, located near the patients in such a way that the distant terminal implements an automatism applying the monitoring rules to the medical data provided to the terminal by at least one sensor that belongs to the patient and/or by a man-machine interface of the distant terminal and/or by a man-machine interface of a networked station and/or by the network according to a method that conforms to one of the preceding embodiments.

The invention also relates to a health monitoring terminal aiming to make it possible to implement a medical diagnosis established by a medically-qualified person concerning a remotely-monitored patient, in particular at his home, and monitored by a communications network, characterised in that:

A server including means for the medically-qualified person to associate medical data with health actions in a server via monitoring rules, the terminal, located near the patient, includes means to be programmed by the server in such a way that this distant terminal implements an automatism applying the monitoring rules to the medical data that is provided to it by at least one sensor that belongs to the patient and/or by a man-machine interface of the distant terminal and/or by a man-machine interface of a networked station and/or by the network according to a method that conforms to one of the preceding embodiments.

Finally, the invention also relates to a health monitoring system implementing the medical diagnosis. The system makes it possible for users, in particular doctors, to remotely monitor patients, in particular patients maintained in the home. The system includes:
- a data server connected to a communications network, in particular of the Internet type,
- a man-machine interface, in particular installed in computing equipment, connected to the data server via a communications network. The man-machine interface is implemented by the users to:
- select and/or input, in the data server, medical data, in particular of the "vomiting" type,
- input and index health actions, in particular of the "hospitalisation" type, corresponding to medical data,
- configure, using selected medical data, the monitoring rules, presented in particular in the form of SQL queries of the "if symptoms=vomiting and temperature >38.5° C., observation period=24 h health action=check urine" type. The monitoring rules are recorded and indexed with the health actions in the data server.

The man-machine interface is furthermore implemented by the users to:
- input and send alert protocols to the data server, in particular information relative to the contact information of the person to inform in the event that a realised health action would be different from the corresponding monitoring rule.

The system furthermore includes:

means of analysis used to analyse the compatibility of the protocols thus sent, in particular the compatibility over time between the new monitoring rules and the former monitoring rules.

The system furthermore includes:

a distant terminal, located with the patients, in particular with the patients that are maintained in the home. The distant terminal is connected to sensors, in particular to medical measuring devices, providing medical data to the distant terminal, and/or the distant terminal receives the medical data from the users and/or the patients via a man-machine interface of the distant terminal, used by the users and/or by the patients to input the medical data.

The system furthermore includes means of programming in order to program automatisms in the distant terminal, from the data server via the communications network. The automatisms are programmed using medical data and health actions indexed in the data server.

The distant terminal includes means for activating automatisms thus programmed in order to:

apply, periodically, the monitoring rules to the medical data provided to the distant terminal by generating health actions to be executed, check the execution, by the users, of health actions, generate alerts in the event the health actions are not executed by the users.

The system thus makes it possible to compile a personalised diagnosis base for each patient and to generate the triggering of appropriate alerts.

3.1 Properties

Health Surveillance Assisted by Diagnosis (HSAD) is a method allowing the use of medical diagnosis for configuring monitoring functions of an alert generator on a patient. It makes use of the notion of "health monitoring rules" which describes the recommended health action (care, medical prescriptions, additional tests, hospitalisation, etc.) following medical observations (readings, symptoms, clinical exam results, etc.), in particular performed on clinical cases or with the patient himself, materialised by the recording of measurements, codes or strings of words: the "medical data".

This method includes on one hand, control for a mechanism for triggering alerts with a check on the conformity of the health action with the medical data on a "patient machine" (PM). It includes, on the other hand, the programming of this automatism using the analysis of the data of the medical records via a specific man-machine interface (MMI) that can be accessed via a network of the Internet type. Finally, the method includes the processing and the making at the disposal on the network of data by a server so as to provide consistent management for the medical rules (review, congruence, etc.) by all of the users.

The general mechanism of the HSAD is based on the coupling between the data and the health actions, making it possible to direct the control on the implementation of actions and not directly on the value of the data. It is therefore regarding a generalisation of sensor control: if the absence of nursing personnel prevents the health actions suggested by the sensor data, the alert protocol is triggered. Inversely, the HSAD makes it possible to take into account a wider range of observations as well as the response provided by the caregivers, and therefore to flexibly regulate the process of triggering alerts. Furthermore, with a health action being conditioned to the probability of simultaneous presence of several pieces of data, the HSAD makes it possible to overcome the continuous systematic measurement of a variable and in particular to take into account the information contained in a syntactical expression. Another characteristic of the HSAD is the evaluation of the effectiveness of the monitoring rules in processing the data and in alerting, if needed, the members of the network of the need to create new rules. This self-control loop allows the diagnosis base of the patient to be enriched. Finally, the HSAD makes it possible in the network to update medical rules and remote monitoring for the patient. The MMI includes in particular assistants that facilitate updating rules.

Use of the HSAD requires, on the patient's end, to have a specific active and communicating machine (PM), equipped with memory for storing data and the automatism and, on the care givers' end and/or concerning other users, to access the MMI on a networked computer station or on a PM.

3.2 Transformation of the Diagnosis into Rules

The user uses a MMI installed on a networked computing station or on a PM and enters into communication with the data server by logging in. The server verifies that the authentication codes correspond to a declared user.

Once connected to the server, the user must select the data on which he is basing his diagnosis and logs the health actions that are to be performed. For each health action, the user specifies the possible care alternatives. The MMI records the health actions on the server and indexes them with the data in the database, which is for example of the relational type.

Illustration of indexing:

Antecedents (data): vomiting symptoms, abdominal pain, alteration in the state of consciousness, high temperature readings for 24 hours, exam indicating acetonuria.

Diagnosis: hyperglycaemia.

Health action: hospitalisation.

In a second time, the user uses the MMI to translate the data selection into monitoring rules in the form of a test on the data (in the form of a SQL query, for example) that he can simulate and modify. If needed, he can use examples of server rules, and modify or render inoperative rules that are active. The user also specifies a period of observation which conditions the collection of data on which the rule is to be applied. The rules are then saved on the server and indexed into the health actions. So, a monitoring rule is made up of tests on a collection of data and health actions.

Illustration of a health rule: if "Symptoms=vomiting" and "Temperature >38.5° C.", "observation period=24 h", "health action=check urine"

The last step consists of using the MMI to send information concerning the alert protocol to the server, i.e. the contact information of the persons to inform as well as the means of transmission used (telephone, SMS, email, etc.) in the event where the realised health action would be different from what the rule recommends. Different alert protocols can be scheduled according to the differences in realisation that are observed.

Each step can be performed at a later moment, independent of the others.

An alternative to the above process is the automatic production of monitoring rules by the server by using known data analysis methods (statistics, neuronal, etc.) or expert systems in decision-making assistance.

3.3 Programming the Automatism

After recording the monitoring rules and the alert protocols, the server performs an ambiguity check in order to verify compatibility between the new and former protocols and rules. If there is ambiguity, the server sends an alert to the user.

The server then generates a code in the language of the PM using a library where the languages of the various machines that can be connected to the network are referenced.

Updating of the PM control automatism takes place via the network either by consulting the server (PULL) or by the server sending the code (PUSH).

3.4 Generation of Alerts by the "Patient Machine" (PM)

The automatism will process the medical data and the health actions stored in the memory of the PM. The memory stores the flow of data coming from the PM's communication ports, from the computer communications network as well as from the man-machine interface that belongs to the patient machine PM (MMIPM) used for manual local input of medical observations and health actions. Data retention time in the memory is conditioned by the monitoring rules.

In a first time, the automatism periodically applies the monitoring rules to the medical data in the memory. If the test is positive, it checks that the planned health actions for each rule are scheduled in the memory of the PM. If they are not, the automatism logs in memory one or several health actions to be validated by applying the rule.

Illustration:
Observations from the nurse in the morning: nausea, abdominal pain, coloured urine;
Health action carried out: stool care, anti-vomiting.
Observations from the nurse in the evening: T=39° C., difficulty speaking;
Health action carried out: paracetamol, message to doctor.
PM logs a Health Action to be validated: transfer to hospital for hyperglycaemia within 2 h.

In a second time, the automatism checks that the times for the scheduled health actions have not passed and that the information concerning their care are in conformity with the schedule. If not, the machine executes the alert protocol by sending messages via one of the means of communication available to the PM. It is therefore not necessary that the PM be constantly connected to a computer network as long as another means of communication is available.

Illustration:
The health action "to be validated" has not been carried out after 2 hours:
The PM sends a pre-recorded message to the Emergency Medical Assistance by telephone.

Once processed by the automatism, the local data (sensor readings, medical observations, etc.) and the alerts can be sent to the data server by the computing network in order to be archived.

3.5 Conclusions

The diagnosis base established for a patient serves therefore as a decision system in order to best trigger alerts in the absence of caregivers. This base avoids the complexity of an expert system by capitalising on the expertise acquired via the socio-medical network on a given patient. The ambiguity analysis, bringing to light possible inconsistencies between the data and the health actions, makes it possible for caregivers to be aware, where applicable, of malfunctions in caring for the patient in the network and to take corrective action. The HSAD method potentially applies to usage on a wide range of machines destined for patient monitoring, for example: a home station, a PDA (Personal Digital Assistant) on the patient or even a programmable beacon.

Figure 1:
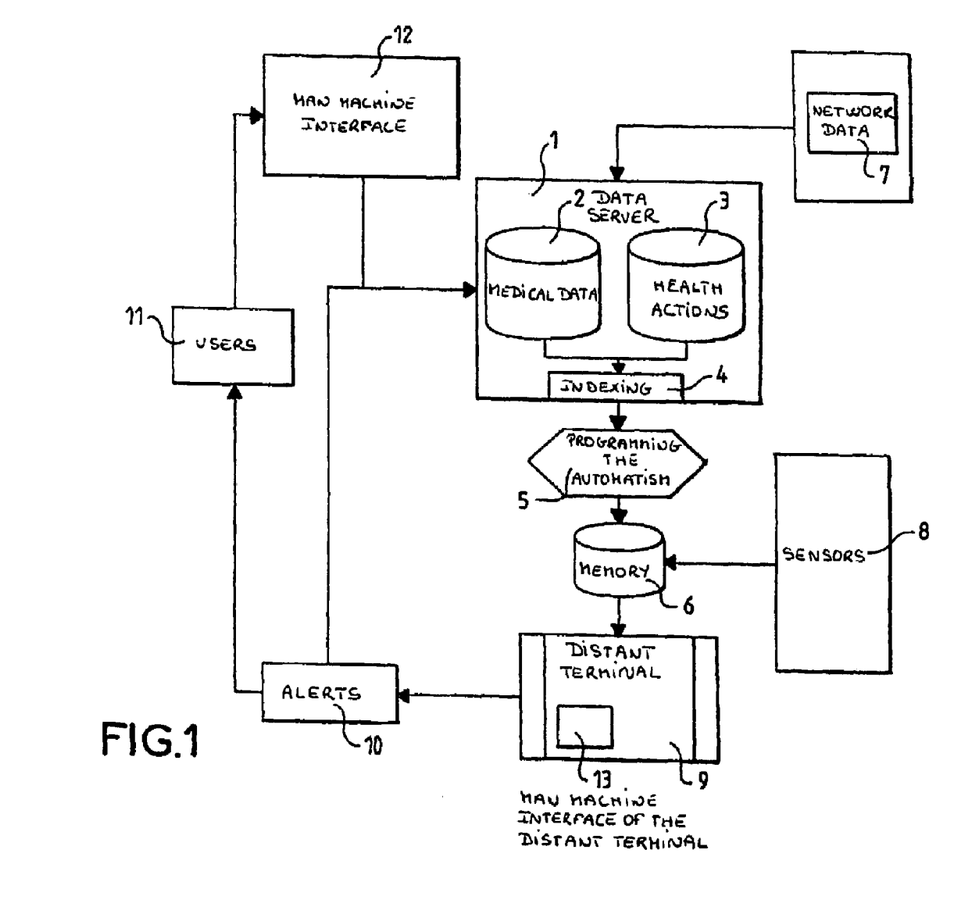
FIG. 1 shows a schematic view of the system according to the invention.

The marked numeric references correspond to the following elements:
1 Data server
2 Medical data
3 Health actions
4 Indexing
5 Programming the automatism
6 Memory
7 Network data
8 Sensors (medical devices)
9 Distant terminal (patient machine)
10 Alerts
11 Users
12 Man-machine interface
13 Man-machine interface of the distant terminal (patient machine)

Note that the user in the sense of the invention can be a patient remotely monitored and/or a medically-qualified person and/or a person authorised to access the system. According to the authorisation level of this user, the latter enters data and/or associates data with health actions using the distant terminal and/or network and/or networked station.

Also note that a patient, in the sense of the invention, is a person who has recourse to a socio-medical service, in particular recourse to one or more professionals that are independent and/or report to a health care institution, independent to any consideration relative to the existence of a health problem and/or to the seriousness of this possible problem.

The invention claimed is:

1. A health monitoring system implementing a medical diagnosis, said system making it possible for users, in particular doctors, to remotely monitor patients, in particular patients maintained in the home, said system including:
  a data server connected to a communications network, in particular of the Internet type;
  a first man-machine interface, in particular installed in computing equipment, connected to said data server via said communications network, said first man-machine interface being implemented by the users to:
    select and/or input, in said data server, medical data, in particular of the "vomiting" type;
    input and index health actions, in particular of the "hospitalisation" type, corresponding to said medical data;
    configure, using said selected medical data, the monitoring rules, presented in particular in the form of SQL queries of the "if symptoms=vomiting and temperature>38.5° C., observation period=24h health action=check urine" type, said monitoring rules being recorded and indexed with said health actions in said data server; and
    input and send alert protocols to said data server, in particular information relative to the contact information of the person to inform in the event that a realised health action would be different from the corresponding monitoring rule;
  means of analysis for analyzing the compatibility of said protocols thus sent, in particular the compatibility over time between the new monitoring rules and the former monitoring rules;

a distant terminal, located with said patients, in particular with said patients that are maintained in the home; said distant terminal being connected to sensors, in particular to medical measuring devices, providing medical data to said distant terminal, and/or said distant terminal receiving said medical data from said users and/or said patients via a second man-machine interface of said distant terminal; and means of programming in order to program automatisms in said distant terminal, from said data server via said communications network, said automatisms being programmed using said medical data and said health actions indexed in said data server;

said distant terminal including means for activating said automatisms thus programmed in order to:

apply, periodically, said monitoring rules to said medical data provided to said distant terminal by generating health actions to be executed, check the execution, by said users, of said health actions, and generate alerts in the event said health actions are not executed by said users;

wherein the system makes it possible to compile a personalised diagnosis base for each patient and to generate the triggering of appropriate alerts.

2. A health monitoring system implementing a medical diagnosis, said system making it possible for users to remotely monitor patients, including:

a data server connected to a communications network;

a first man-machine interface connected to said data server via said communications network, said first man-machine interface being implemented by the users to:

select and/or input, in said data server, medical data;

input and index health actions corresponding to said medical data;

configure, using said selected medical data, the monitoring rules, presented in the form of SQL queries, said monitoring rules being recorded and indexed with said health actions in said data server; and input and send alert protocols to said data server in the event that a realised health action would be different from the corresponding monitoring rule;

a distant terminal, located with said patients; said distant terminal being connected to sensors providing medical data to said distant terminal, and/or said distant terminal receiving said medical data from said users and/or patients via a second man-machine interface of said distant terminal;

means of programming in order to program automatisms in said distant terminal, from said data server via said communications network, said automatisms being programmed using said medical data and said health actions indexed in said data server; and means for activating said automatisms programmed in said distant terminal in order to:

apply, periodically, said monitoring rules to said medical data provided to said distant terminal by generating health actions to be executed;

check the execution, by said users, of said health actions; and generate alerts in the event said health actions are not executed by said users, wherein the system makes it possible to compile a personalised diagnosis base for each patient and to generate the triggering of appropriate alerts.

3. A health monitoring system implementing a medical diagnosis, said system making it possible for users to remotely monitor patients, including:

a data server connected to a communications network;

a first man-machine interface connected to said data server via said communications network, said first man-machine interface being implemented by the users to:

configure, using selected medical data and health actions input in said data server, monitoring rules in order to recommend one of the health actions, presented in the form of SQL queries, said monitoring rules being recorded in said data server; and input and send alert protocols to said data server in the event that a realised health action would be different from a corresponding monitoring rule;

a distant terminal, located with said patients, said distant terminal being connected to sensors providing medical data to said distant terminal, and/or said distant terminal receiving said medical data from said users and/or said patients via a second man-machine interface of said distant terminal;

means of programming in order to program automatisms in said distant terminal, from said data server via said communications network in said data server; and means for activating said automatisms programmed in said distant terminal in order to:

apply, periodically, said monitoring rules to said medical data provided to and/or received by said distant terminal in order to recommend health actions to be executed; and generate alerts in the event said recommended health actions are not executed by said users, wherein the system makes it possible to generate the triggering of appropriate alerts.

4. A health monitoring system implementing a medical diagnosis, said system making it possible for users to remotely monitor patients, including:

data saving means connected to a communications network, a first man-machine interface connected to said data saving means via said communications network, said first man-machine interface being implemented by the users to:

configure, using selected medical data and health actions input in said data saving means, monitoring rules in order to recommend one of the health actions, presented in the form of SQL queries, said monitoring rules being recorded in said data saving means; and input and send alert protocols to said data saving means in the event that a realised health action would be different from the corresponding monitoring rule;

a distant terminal, located with said patients, said distant terminal being connected to sensors providing medical data to said distant terminal, and/or said distant terminal receiving said medical data from said users and/or said patients via a second man-machine interface of said distant terminal;

means of programming in order to program automatisms in said distant terminal, from said data saving means via said communications network in said data saving means; and means for activating said automatisms programmed in said distant terminal in order to:

apply, periodically, said monitoring rules to said medical data provided to and/or received by said distant terminal in order to recommend health actions to be executed; and generate alerts in the event said recommended health actions are not executed by said users, wherein the system makes it possible to generate the triggering of appropriate alerts.

5. A health monitoring method implementing a medical diagnosis making it possible for users to remotely monitor at least a patient, including the following steps:

configuring monitoring rules using medical data and health actions;

obtaining alert protocols;

obtaining medical data by a distant terminal located with said patient, said obtained medical data being medical data measured by sensors and provided to said distant terminal, or medical data received from said users and/or said patient via a first man-machine interface of said distant terminal;

applying, periodically, said monitoring rules to said medical data obtained by said distant terminal in order to recommend health actions to be executed; and generating at least an alert, taking into account at least one of said alert protocols, in the event said recommended health actions are not executed by said users.

6. The health monitoring method according to claim 5, wherein the step of configuring is implemented by the users by use of a second man-machine interface, connected to a data server via a communications network, said monitoring rules being recorded and indexed with said health actions in said data server, and wherein in the step of obtaining alert protocols, the alert protocols, in the event that a realised health action would be different from the corresponding monitoring rule, are input and sent to said data server, and wherein the step of applying said monitoring rules and the step of generating at least an alert are implemented by automatisms being programmed using said medical data and said health actions indexed in said data server, provided in said distant terminal, activated by said distant terminal.

7. The health monitoring method according to claim 5, further including:

analysing the compatibility of said alert protocols thus obtained.

8. The health monitoring method according to claim 5, further including:

selecting and/or inputting medical data in a data saving means; and inputting and indexing health actions, such that it is possible to compile a personalised diagnosis base for each patient.

9. Computer program product downloadable from a communication network and/or stored on a medium that can be read by computer and/or executed by a microprocessor comprising program code instructions for implementing the health monitoring method according to claim 5 when said program is executed on a computer.

10. A method of health monitoring implementing a medical diagnosis established by a medically-qualified person concerning a remotely-monitored patient, in particular at his home, and monitored via a communications network, comprising:

associating by the medically-qualified person medical data with health actions in a server via monitoring rules;

programming a distant terminal, located near the patient in such a way that the distant terminal implements an automatism applying the monitoring rules to the medical data provided to the terminal by a sensor associated with the patient and/or by a first man-machine interface of the distant terminal and/or by a second man-machine interface of a networked station and/or by the network; and applying by said automatism at least one of said monitoring rules to at least one of the medical data provided to said distant terminal by said first man-machine interface of the distant terminal, where said at least one of the medical data has been input by said medically-qualified person, in order to associate with said at least one of the medical data a health action to be executed, and generate an alert in the event said health action to be executed is different from the health action executed by at least a user.

11. The method according to claim 10, wherein in the step of applying, said at least one of the medical data input by said medically-qualified person is information contained in a syntactical expression following a medical observation.

12. The method according to claim 11, wherein said syntactical expression following a medical observation under consideration is selected from the group consisting of: intensity of pain, state of fatigue, alterations in the state of consciousness, and difficulties in speaking.

13. The method according to claim 10, wherein in the step of associating, at least a first data provided by a sensor and at least a second data in the form of information contained in a syntactical expression following a medical observation are associated with an health action.

14. The method according to claim 10, further comprising:

saving said medical data, said health actions, and said monitoring rules onto a server connected to said communication network.

15. The method according to claim 14, further comprising:

sending at least one of said medical data provided by a sensor that belongs to the patient and/or by the first man-machine interface of the distant terminal and/or by the second man-machine interface of the networked station and/or by the network to the medically-qualified person via said communication network so that the latter takes into account this data sent in order to possibly modify the monitoring rules associating data and health actions at the level of the server.

16. The method according to claim 10, characterized in that the sensors under consideration are configured to measure data that is selected from the group consisting of: blood pressure, heart rhythm, body temperature, skin temperature, sodium content on the skin, kinetic and/or kinematic parameters of the body, blood dosage, analysis of urine and/or stool and/or blood gas, weight, electrocardiogram data, heart sounds, oxygen saturation, and thermal image.

17. The method according to claim 10, characterized in that the data provided by the network is related to results of biological examinations and/or functioning of a piece of equipment connected to the network, in particular home automation equipment for detecting presence, control of access, heating, lighting, openings, fire, flooding, mains cut-off and/or a medical device, related to an alarm signal or any signal resulting from the transformation of measurements and coming from such a connected device, in particular a pump and/or administration set and/or respirator and/or fall detector, or related to information coming from third-party software, in particular from an expert system, likely to be executed on the terminal or on a machine connected to the terminal, such as software for monitoring self-care haemodialysis and/or for monitoring glycaemia of diabetics and/or monitoring blood pressure.

18. Computer program product downloadable from a communication network and/or stored on a medium that can be read by computer and/or executed by a microprocessor comprising program code instructions for implementing the method of health monitoring according to claim 10 when said program is executed on a computer.

19. A health monitoring server configured to implement a medical diagnosis established by at least a medically-qualified person concerning a remotely-monitored patient, in particular at his home, and monitored by a communications network, comprising:

means for associating medical data with health actions via monitoring rules for use by the medically-qualified person;

means for programming a distant terminal, located near the patient in such a way that the distant terminal implements an automatism applying the monitoring rules to the medical data provided to the terminal by at least one sensor that belongs to the patient and/or by a first man-machine interface of the distant terminal and/or by a second man-machine interface of a networked station and/or by the network, said automatism applying at least a monitoring rule to the medical data provided to the terminal by said first or second man-machine interface where said medical data was input by said medically-qualified person, in order to associate with said medical data a health action to be executed, and generate an alert in the event said health action to be executed is different from the health action executed by at least a user; and means for saving said medical data, said health actions, and said monitoring rules.

20. A health monitoring terminal configured to implement a medical diagnosis established by a least a medically-qualified person concerning a remotely-monitored patient, in particular at his home, and monitored by a communications network, comprising:

a first man-machine interface; and an automatism implemented with medical data that are provided by at least one sensor that belongs to the patient and/or by a second man-machine interface of a distant terminal located near the patient and/or by a third man-machine interface of a networked station and/or by the network, said automatism applying at least a monitoring rule to the medical data provided to the terminal by said second or third man-machine interface, where said medical data was input by said medically-qualified person; in order to associate with said medical data a health action to be executed, and generate an alert in the event said health action to be executed is different from the health action executed by at least a user.

\* \* \* \* \*

UNITED STATES PATENT AND TRADEMARK OFFICE
CERTIFICATE OF CORRECTION

| | | |
|---|---|---|
| PATENT NO. | : 7,552,101 B2 | Page 1 of 1 |
| APPLICATION NO. | : 10/577499 | |
| DATED | : June 23, 2009 | |
| INVENTOR(S) | : Bruno Bleines | |

It is certified that error appears in the above-identified patent and that said Letters Patent is hereby corrected as shown below:

Title Page, Item (73) Assignee: delete "Vigimedia S.A.S." insert --Vigimedis S.A.S.--

Signed and Sealed this
Twenty-third Day of August, 2011

David J. Kappos
*Director of the United States Patent and Trademark Office*